(12) United States Patent
Ursella et al.

(10) Patent No.: US 10,914,691 B2
(45) Date of Patent: Feb. 9, 2021

(54) METHOD AND APPARATUS FOR NON-DESTRUCTIVE INSPECTION OF FRUITS HAVING AN AXIS OF ROTATIONAL SYMMETRY

(71) Applicant: MICROTEC S.R.L., Bressanone (IT)

(72) Inventors: Enrico Ursella, Mestre (IT); Giancarlo Zane, Mestre (IT); Marco Boschetti, Levico Terme (IT); Simone Faccini, Bolzano (IT)

(73) Assignee: MICROTEC S.R.L., Bressanone (IT)

( * ) Notice: Subject to any disclaimer, the term of this patent is extended or adjusted under 35 U.S.C. 154(b) by 143 days.

(21) Appl. No.: 16/264,162

(22) Filed: Jan. 31, 2019

(65) Prior Publication Data
US 2019/0242833 A1    Aug. 8, 2019

(30) Foreign Application Priority Data
Feb. 5, 2018 (IT) .................. 102018000002420

(51) Int. Cl.
*G06T 7/11* (2017.01)
*G01N 23/083* (2018.01)
(Continued)

(52) U.S. Cl.
CPC ......... *G01N 23/083* (2013.01); *B07C 5/3416* (2013.01); *G01N 23/04* (2013.01);
(Continued)

(58) Field of Classification Search
CPC .... G01N 23/083; G01N 33/025; G01N 23/18; G01N 23/04; G01N 2223/401;
(Continued)

(56) References Cited

U.S. PATENT DOCUMENTS

| 3,768,645 A | 10/1973 | Conway et al. |
| 4,528,680 A * | 7/1985 | Archambeault ...... G06M 1/101 209/551 |

(Continued)

*Primary Examiner* — Sheela C Chawan
(74) *Attorney, Agent, or Firm* — Pearne & Gordon LLP

(57) ABSTRACT

This disclosure relates to a method for non-destructive inspection of a fruit (1) having an axis of rotational symmetry (10). The method comprises the step of positioning the fruit (1) in such a way that its axis of rotational symmetry (10) has an orientation that is substantially parallel to a predetermined plane (20) and the step of radiographing the fruit (1), where the direction of emission of X-rays is substantially perpendicular to said predetermined plane (20) and an X-ray image obtained (41) lies on said predetermined plane (20). The X-ray image obtained (41) is processed to calculate, at corresponding points of the X-ray image (41), respective values of attenuation of the X-ray signal through the fruit (1). The X-ray image (41) is divided into a plurality of sections (415) which are perpendicular to the projection (410) of the axis of rotational symmetry (10) on the predetermined plane (20). Each section (415) is the projection of a corresponding slice of the fruit (1) that is substantially perpendicular to the axis of rotational symmetry (10). For each section (415), the deviation between a signal attenuation trend obtained from processing the X-ray image and a reference trend, or the deviation between a trend of a local coefficient of average attenuation obtained from processing the X-ray image and a trend with constant value, is examined in order to identify any anomalies, discontinuities or variations which are indicative of respective non-uniformities in the corresponding slice of fruit. This disclosure also relates to an apparatus (9) for carrying out a non-destructive inspection of a fruit (1) having an axis of rotational symmetry (10), said apparatus being configured for implementing the method according to the disclosure.

16 Claims, 4 Drawing Sheets

(51) Int. Cl.
*G01N 23/18* (2018.01)
*G01N 23/04* (2018.01)
*B07C 5/34* (2006.01)
*G06T 7/00* (2017.01)
*G01N 33/02* (2006.01)
*G06T 7/68* (2017.01)

(52) U.S. Cl.
CPC ........... *G01N 23/18* (2013.01); *G01N 33/025* (2013.01); *G06T 7/001* (2013.01); *G06T 7/0004* (2013.01); *G06T 7/11* (2017.01); *G06T 7/68* (2017.01); *B07C 2501/009* (2013.01); *G01N 2223/401* (2013.01); *G01N 2223/618* (2013.01); *G06T 2207/10116* (2013.01); *G06T 2207/30128* (2013.01)

(58) Field of Classification Search
CPC ............ B07C 5/3416; B07C 2501/009; G06T 7/0004; G06T 7/68; G06T 7/11; G06T 7/001; G06T 2207/10116; G06T 2207/30128
USPC ....... 382/100, 108, 110, 141, 143, 151, 149, 382/173, 181, 190, 216, 254, 31; 56/340.1
See application file for complete search history.

(56) References Cited

U.S. PATENT DOCUMENTS

| | | | | |
|---|---|---|---|---|
| 5,026,982 A * | 6/1991 | Stroman | .................. | B07C 5/10 250/221 |
| 5,589,209 A * | 12/1996 | Mizrach | ................ | G01N 29/07 426/231 |
| 5,726,750 A * | 3/1998 | Ito | ........................ | G01N 21/359 209/587 |
| 5,751,833 A * | 5/1998 | Blit | ....................... | B07C 5/3422 209/576 |
| 6,334,092 B1 * | 12/2001 | Hashimoto | ............ | G01N 21/27 356/328 |
| 7,860,214 B1 | 12/2010 | Haff | | |
| 8,284,895 B1 | 10/2012 | Haff | | |
| 9,129,277 B2 * | 9/2015 | MacIntosh | ................ | G06T 7/0004 |
| 2004/0247193 A1 * | 12/2004 | Qualtrough | ........... | B07C 5/3422 382/243 |

\* cited by examiner

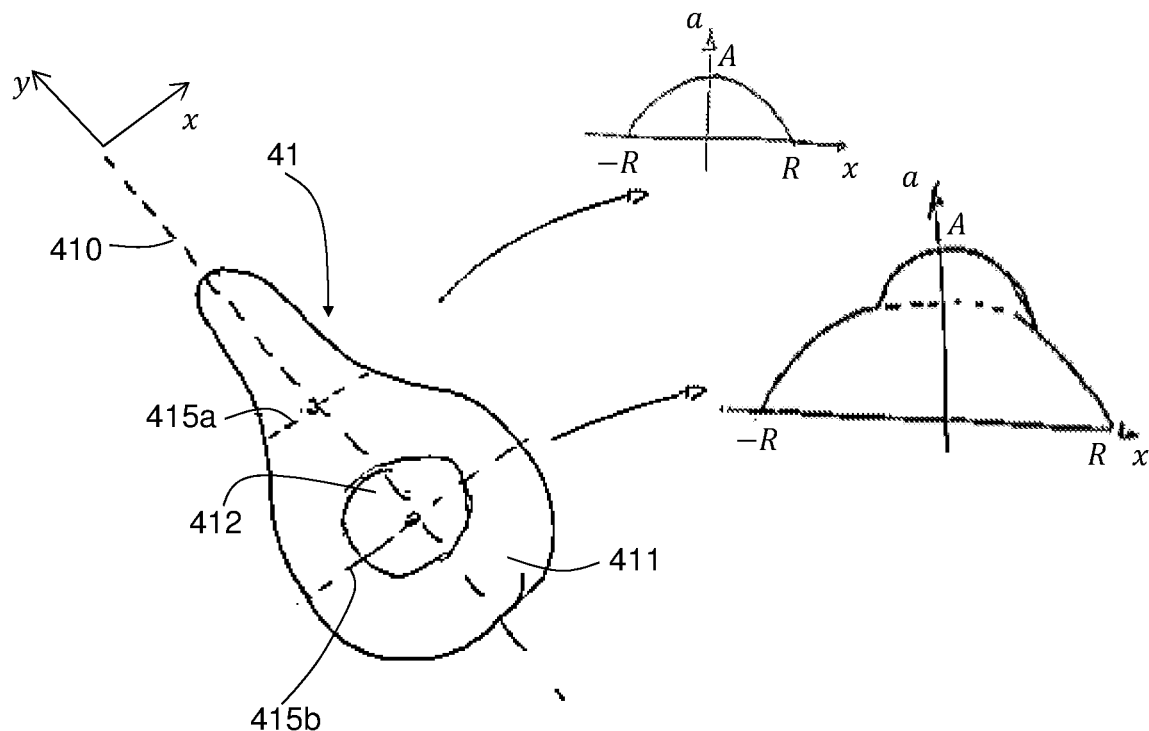
FIG. 4
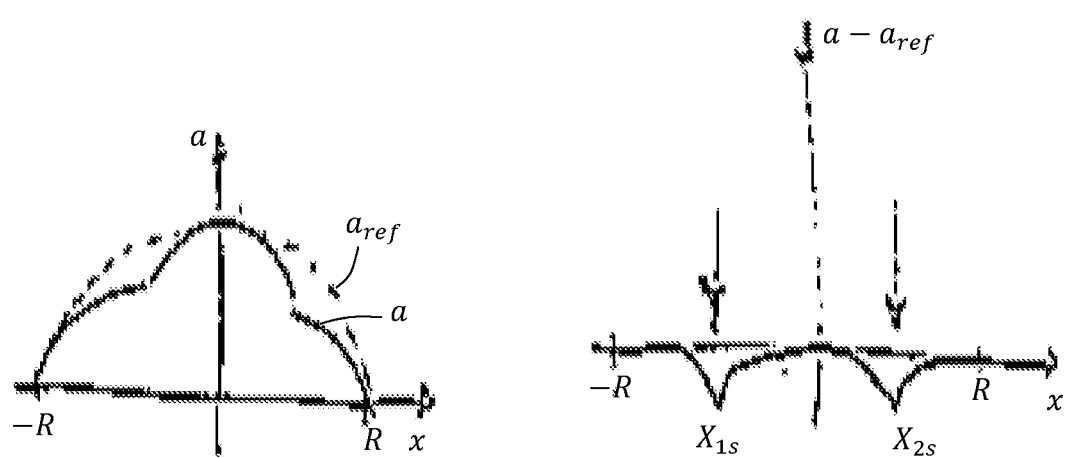
FIG. 5      FIG. 6

METHOD AND APPARATUS FOR NON-DESTRUCTIVE INSPECTION OF FRUITS HAVING AN AXIS OF ROTATIONAL SYMMETRY

CROSS-REFERENCE TO RELATED APPLICATIONS

The present application claims priority to Italian Patent Application No. 102018000002420 filed on Feb. 5, 2018, which is incorporated herein by reference in its entirety.

DESCRIPTION

This disclosure relates in general to the sector of apparatuses for the food sector. Specifically, this disclosure relates to a method for non-destructive inspection of a fruit having an axis of rotational symmetry. This disclosure also relates to an apparatus for carrying out that non-destructive inspection.

There are prior art apparatuses which, using X-rays, allow a check for the possible presence of unwanted bodies (such as pieces of seeds/stones or other items) in processed fruit or for checking some types of internal damage in fruits.

As an alternative to the prior art methods, this disclosure proposes a method for non-destructive inspection specifically intended for fruits which have an axis of rotational symmetry, such as avocados, citrus fruits, apples, and allows the identification of internal characteristics of such fruits.

That is achieved by a method for non-destructive inspection as in the appended claims, as well as by an apparatus as claimed.

In comparison with the prior art methods, the method according to this disclosure is an alternative method which may be easier to apply and which may provide more precise results.

Specifically, the method according to this disclosure is useful because it makes use of the rotational symmetry of the fruit and avoids the complication of explicitly determining the three-dimensional shape of the fruit itself, which in contrast is required in some prior art methods.

According to one aspect of this disclosure, the fruit is positioned in such a way that its axis of rotational symmetry is substantially parallel to a plane on which an X-ray image is generated. The X-ray image obtained in this way is therefore symmetrical relative to a projection of the axis of rotational symmetry of the fruit. By dividing the X-ray image into sections or strips which are perpendicular to the projection of the axis of rotational symmetry, each of said sections or strips is a projection of a respective substantially circular slice of fruit.

It should be noticed that the total attenuation along the path of each X-ray depends both on the length of the stretch of fruit passed through, and the absorption coefficient (or attenuation coefficient) of the substance passed through. If the substance is uniform (for example, only the flesh of the fruit), the total attenuation is the attenuation coefficient of the substance multiplied by the length of the stretch passed through; if the substance is not uniform (for example, for a stretch which comprises flesh, stone and/or decay), the total attenuation is the sum of the attenuations in the individual uniform stretches passed through.

According to a first alternative of the method according to this disclosure, it is possible to identify where the fruit has discontinuities and/or non-uniformities by means of a comparison between the attenuation of the X-ray signal which is actually detected at the individual points of each section or strip of X-ray image and the attenuation which would be expected if the corresponding circular slice were to have a uniform attenuation coefficient.

According to a second alternative of the method according to this disclosure, it is possible to identify where the fruit has discontinuities and/or non-uniformities by calculating a local coefficient of average attenuation in the different zones of the X-ray image and searching for the deviations or the variations of the local coefficient of average attenuation (calculated in that way) relative to a trend with constant value. The local coefficient of average attenuation can be calculated at each point by dividing the X-ray signal attenuation which is actually detected at the point by the length of the respective stretch of fruit passed through, where the length can be calculated by assuming that the corresponding slice is circular. In practice, that local coefficient of average attenuation is an average value for the specific stretch of fruit passed through. The two alternatives described above share the same concept of considering each of those sections or strips of the X-ray image as the projection of a respective substantially circular slice of fruit. The two alternatives differ due to the examination of overall attenuation for the whole stretch passed through (first alternative) or the examination of the local coefficient of average attenuation in the stretch passed through (second alternative). Basically, they differ in a step of the mathematical processing, but are based on a same general concept.

The method according to this disclosure is usable, for example, for searching for the size of a stone in a fruit, in particular in an avocado.

The method according to this disclosure is usable, for example, for checking if the stone (in particular the stone of an avocado) is detached from the flesh of the fruit.

The method according to this disclosure is usable, for example, for checking if the peel is detached from the flesh of the fruit, in particular for a fruit which is a citrus fruit, such as a mandarin.

Therefore, the method according to this disclosure is useful for assessing the edible fruit percentage, determining the size of the stone and/or the peel, and/or for identifying any anomalies such as zones of decay. Therefore, it allows assessment of the quality of a fruit using objective criteria and in a non-destructive way.

In particular, it uses the symmetry of the fruit and its contour: for example, by calculating the average coefficient of attenuation in the various zones and analysing the symmetry, the dimensions of the stone, of the peel and of any anomalies can be revealed.

Within the scope of this disclosure, the term "fruit" refers to an object that can be fruit in the conventional sense (specifically drupes, pomes, citrus fruits) or vegetable (for example, tomatoes), which all have an axis of rotation relative to which the object is substantially symmetrical.

Further features and the advantages of the subject of this disclosure are more apparent in the detailed description below, with reference to example, non-limiting embodiments of a method and an apparatus for non-destructive inspection of a fruit. Reference will be made to the accompanying drawings, in which.

Figure 7:
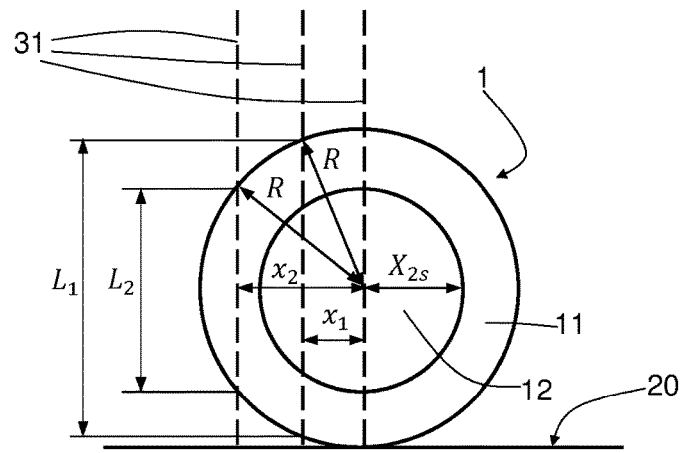
Figures 8, 9, 10:
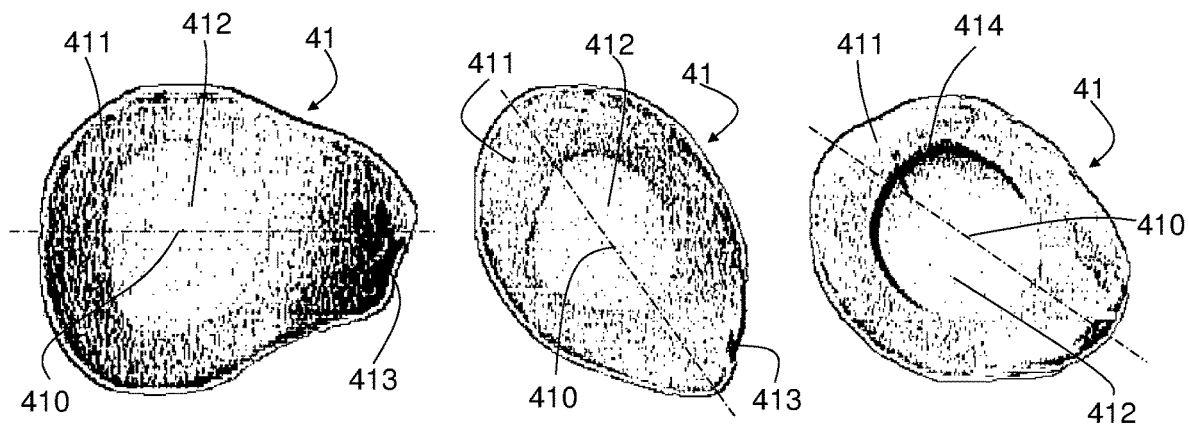
Figure 11:
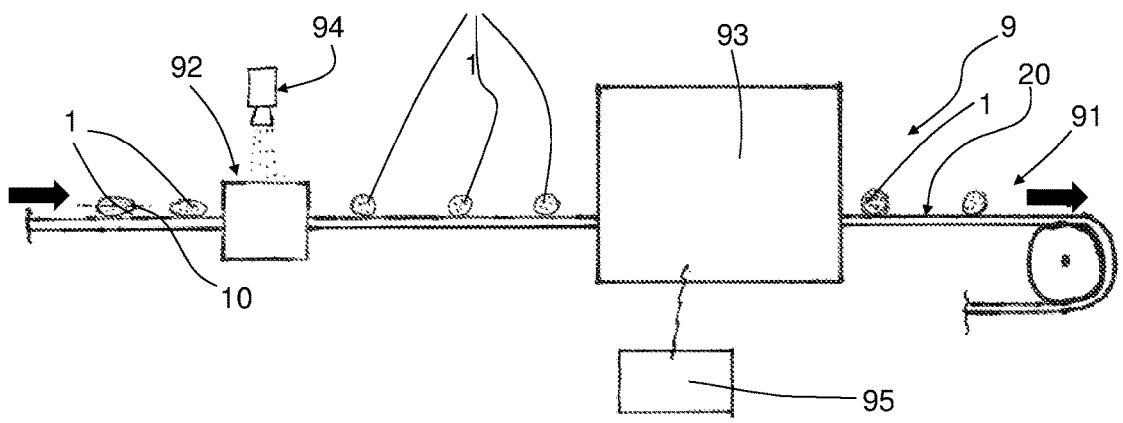
Figure 12:
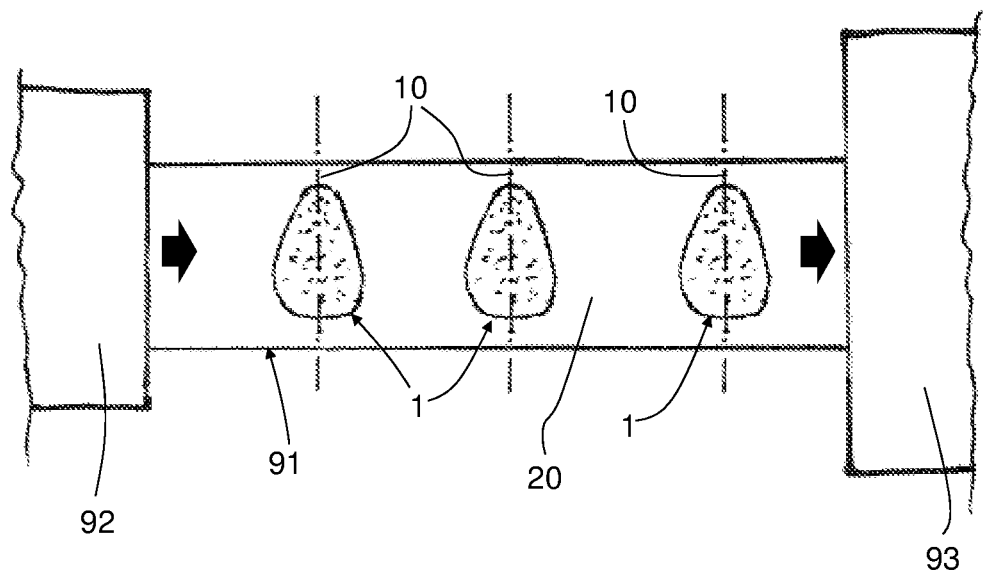

FIGS. 3 to 6 schematically illustrate several processing steps according to a first alternative of the method according to this disclosure;

FIG. 7 is a cross-section of the fruit, sectioned by a plane perpendicular to its axis of rotational symmetry, during a step of the method;

FIGS. 8 to 10 show several examples of images of fruit reworked according to a second alternative of the method according to this disclosure;

FIG. 11 is a schematic and simplified view of a non-destructive inspection apparatus according to this disclosure;

FIG. 12 is a schematic and simplified top view of a portion of the apparatus of FIG. 11.

With reference to the above-mentioned figures, a fruit has been generically labelled with the reference character 1 and an apparatus for carrying out a non-destructive inspection of a fruit has been labelled with the reference character 9. The fruit 1 shown in the figures is, for example, an avocado, but obviously it may be another fruit or vegetable.

The fruit 1 has an axis of rotational symmetry 10, that is to say, for the fruit 1 it is possible to identify an axis 10 relative to which the fruit 1 is substantially symmetrical when it rotates. In practice, if the fruit 1 is cut according to planes orthogonal to the axis 10, the sections obtained are circular sections with their centre on the axis 10. Within the scope of this disclosure, the rotational symmetry must be considered within some tolerance margin, in so far as it allows the level of precision required for the inspection.

In a first step of the method for non-destructive inspection, the fruit 1 is positioned in such a way that its axis of rotational symmetry 10 has an orientation that is substantially parallel to a predetermined plane 20. For example, the predetermined plane 20 is a substantially horizontal plane and the fruit 1 is placed lying in such a way that its axis of rotational symmetry 10 is substantially horizontal. If necessary, for a pear-shaped fruit 1 like an avocado, it would be possible to use a support 2 to hold the fruit 1 with its head raised above the horizontal predetermined plane 20, so that its axis of rotational symmetry 10 is horizontal.

Figure 2:
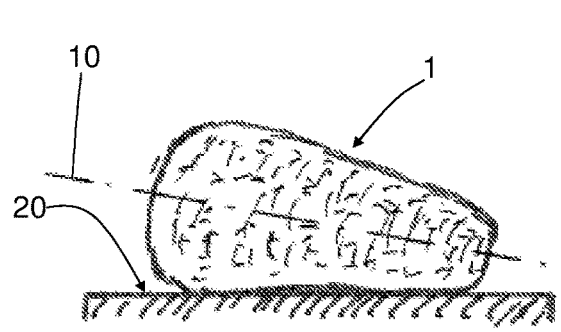
FIG. 2 shows a variant of positioning of the fruit during the step of the method of FIG. 1.

However, it must be considered that the method according to this disclosure may also be successfully applied if the axis of rotational symmetry 10 is not precisely parallel to the predetermined plane 20. For example, an inclination of the axis of rotational symmetry 10 relative to the predetermined plane 20 of up to around 25° could have an insignificant effect on the results and would therefore be acceptable. The expression "substantially parallel" should be understood in that sense. Therefore, the fruit 1 could be simply lying on the horizontal predetermined plane 20, without any support 2, as shown for example in FIG. 2.

Figure 1:
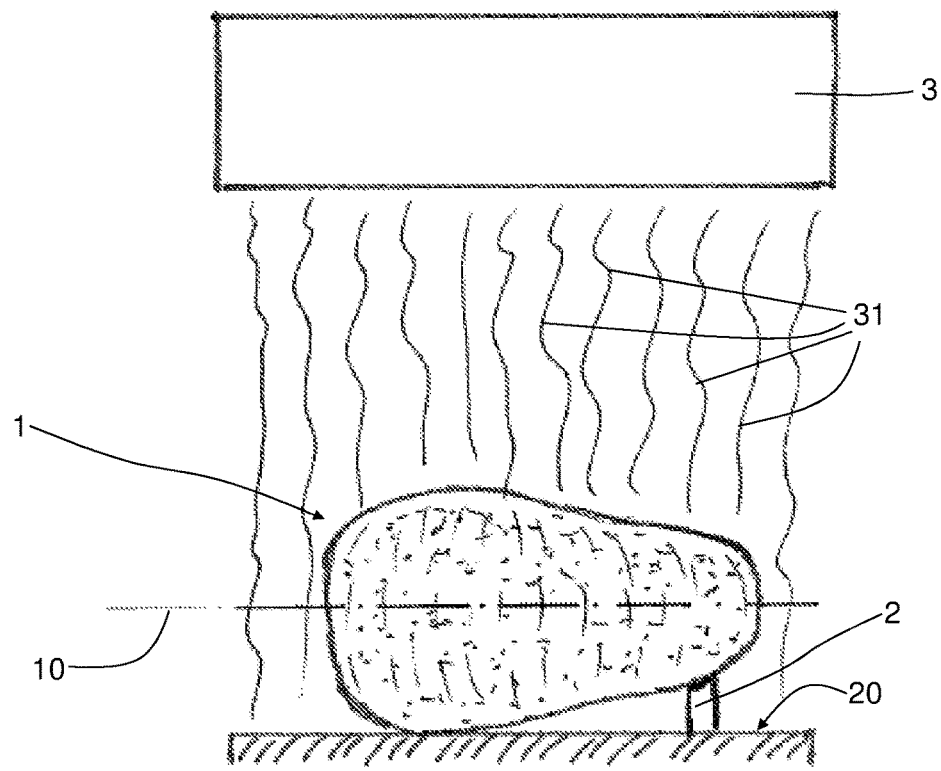
FIG. 1 is a schematic view of a fruit during a step of the method according to this disclosure, in which the fruit is radiographed.

In a second step of the method, the fruit 1 is radiographed. X-rays are emitted with a direction of emission that is substantially perpendicular to the predetermined plane 20 and an X-ray image obtained lies on the predetermined plane 20. In other words, the X-ray image is a projection on the predetermined plane 20 which represents the fruit 1 using X-rays. FIG. 1 schematically illustrates an X-ray emitter 3, which sends a beam of X-rays (which are labelled 31) towards the predetermined plane 20 perpendicularly to the latter. The X-rays strike the fruit 1 and, after having passed through it, are received by a suitable X-ray receiver (not illustrated) positioned parallel to the predetermined plane 20. The X-ray image is constituted of what is received by the X-ray receiver. It is not necessarily a physical image, rather it is an electronic image, and basically is constituted of a matrix of coordinates (x, y) and of the values measured at the respective points having such coordinates.

The X-ray image obtained is then processed (in particular by an electronic processing unit 95) to calculate, at corresponding points of the X-ray image obtained, respective values of attenuation of X-ray signal through the fruit 1. Basically, the X-ray image obtained is converted into an image (also an X-ray image) whose coordinates are associated with the local values of attenuation of the X-rays through the fruit 1: each value represents the attenuation caused by passing through a respective stretch of fruit 1, that is to say, the attenuation along a route between the emitter 3 and a specific point of the image. As shown in FIG. 7, since the fruit 1 is positioned with the axis of rotational symmetry 10 substantially parallel to the predetermined plane 20, a length L of the stretch depends on a distance x of the point from a projection of the axis of rotational symmetry 10 on the predetermined plane 20.

Specifically, the attenuation considered here is a quantity with a logarithmic dependence on the signal measured (that is to say, the intensity of X-rays received at a specific point by the receiver). In particular, the attenuation a at a point x is calculated as $$a(x) = \log\left[\frac{I_e(x) - I_0(x)}{I(x) - I_0(x)}\right],$$

where I(x) is the signal measured at the point x in the presence of the fruit 1, $I_0(x)$ is the signal measured at the point x when the X-ray emitter 3 is switched off, $I_e(x)$ is the signal measured at the point x in the absence of the fruit 1.

Figure 3:
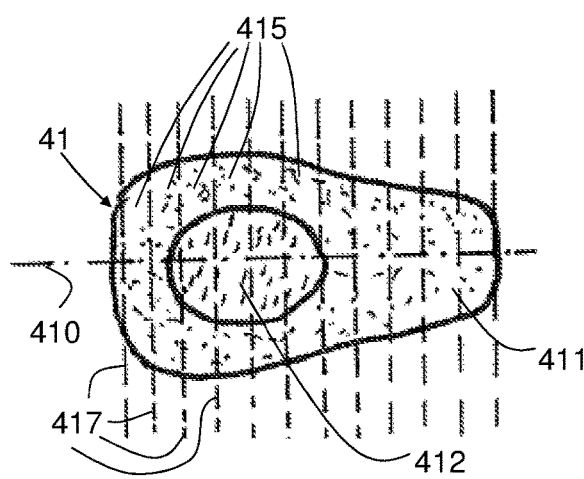

In another processing step, schematically illustrated in FIG. 3, the X-ray image (labelled 41) of the fruit 1 is divided into a plurality of sections 415 which are perpendicular to a projection 410 of the axis of rotational symmetry 10 on the predetermined plane 20. In practice, the sections 415 are delimited by straight lines 417 perpendicular to the projection 410 of the axis of rotational symmetry 10. Therefore, each section 415 is a strip which is a projection of a corresponding slice of the fruit 1 that is substantially perpendicular to the axis of rotational symmetry 10. The width of the sections 415, that is to say, the distance between the straight lines 417, may be selected as desired depending on requirements and is smaller when the resolution to be obtained for the method described herein is higher.

It should be noticed that dividing the X-ray image should not be understood to be a step of physically cutting an image. In fact, that expression simply describes a data processing step which is in any case carried out by a computer. The same applies for the subsequent processing steps. It should also be noticed that the processing may be carried out in an equivalent way on the image expressed in terms of attenuation values rather than in terms of received signal.

Even references to the "slice" of fruit 1 do not mean that the fruit is or will be physically cut into slices. The inspection according to this disclosure is of the non-destructive type and the fruit 1 remains intact. Therefore, the expression "corresponding slice of the fruit" indicates the portion of fruit located between the emitter 3 and the section 415 of X-ray image considered, said portion of fruit having been passed through by the X-rays and projected onto the section 415.

It should be noticed that, thanks to the positioning of the fruit 1 with the axis of rotational symmetry 10 substantially parallel to the predetermined plane 20, each slice is substantially circular and its centre is on the axis of rotational symmetry 10.

The position of the projection 410 of the axis of rotational symmetry 10 in the X-ray image 41 may be known in advance because the fruit 1 has been oriented in a known way, for example with the axis of rotational symmetry 10 perpendicular to a conveying direction in the apparatus 9, as shown in FIG. 12. Alternatively, the position of the projection 410 of the axis of rotational symmetry 10 may be calculated as an axis of symmetry of the X-ray image 41 or as an axis of symmetry of a projection of an outer contour (that is to say, as an axis of symmetry of the projection of the outer surface of the peel) of the fruit 1.

The processing procedure takes into consideration each section 415 and applies to it a sequence of processing sub-steps.

For simple processing, for example, it is possible to consider a median line of the section 415 or a straight line 417 delimiting the section 415 as representing the whole section 415. In practice, considering that the width of the section 415 is small, for each section 415 the processing may consider an attenuation trend only in direction perpendicular to the projection 410 of the axis of rotational symmetry 10, ignoring the variations in direction parallel to the projection 410.

A first mode of carrying out the method is described below.

For each section 415, two end points corresponding to the projection of the outer contour (that is to say, the outer surface of the peel) of the fruit 1 are determined. Each end point is identifiable as a border between a region with null attenuation of the X-ray signal and a region with increasing or decreasing attenuation (depending on the direction along which the section 415 is being examined) of X-ray signal. Indeed, the X-rays are not attenuated if they do not encounter the fruit; the greater the thickness of the fruit that they have to pass through is, the more the X-rays are attenuated. A trend of the attenuation of the X-ray signal between the two end points is obtained from the respective values calculated by processing the X-ray image 41. In other words, said trend is a detected trend.

Then a reference trend of the attenuation of the X-ray signal between the two end points is calculated, adopting an attenuation coefficient having a value that is constant for the corresponding slice. In other words, the reference trend is calculated assuming that the inside of the slice of fruit is uniform and has the same attenuation coefficient throughout. According to this assumption, the attenuation depends only on the length of fruit passed through, which can be precisely calculated considering that the slice is circular.

In particular, the reference trend is calculated as follows:
by determining a radius of the corresponding slice of the fruit: the radius is calculated as half-distance between the two end points of the section 415; it is assumed that the corresponding slice of the fruit has a circular shape with the radius calculated in this way;
for each point between the two end points of the section 415, an attenuation reference value is calculated as $a_{ref}(x) = A \cdot (\sqrt{R^2 - x^2})/R$ where R is the calculated radius, x is a distance of the point from the projection 410 of the axis of rotational symmetry 10, A is a constant, $a_{ref}(x)$ is the attenuation reference value at the point at distance x.

As regards the value of the constant A, it is selected for example as the largest attenuation value for the section 415, as obtained by processing the X-ray image. In practice, it is the attenuation value for the point located on the projection 410 of the axis of rotational symmetry 10.

Once the reference trend of the signal attenuation has been obtained, the deviation between the X-ray signal attenuation trend obtained by processing the X-ray image (that is, the detected trend) and the reference trend is calculated for each point between the two end points. In practice, the values obtained by the measurement are compared with the values calculated assuming that the circular slice is completely uniform.

Finally, the trend of the deviation, between the two end points, is examined in order to identify any anomalies, discontinuities or variations which are indicative of respective non-uniformities in the corresponding slice of fruit. In fact, the deviation is higher the less uniform the corresponding stretch of fruit passed through is.

For example, the method may be intended to identify the dimensions of a central stone 12 of the fruit 1, which in particular is an avocado.

Since the radiodensity of the stone 12 is very different to the radiodensity of the flesh 11, if the slice considered comprises even part of the stone there will be greater attenuation at the latter. That is shown for example in FIG. 3, where the region 412 corresponding to the projection of flesh 11 with stone 12 is distinguishable from the region 411 corresponding to the projection of only flesh 11 (the border between the two regions 411, 412 has been highlighted for clarity).

FIG. 4 shows for example the attenuation trend for two sections 415a, 415b: a first section 415a only relates to flesh 11 and the attenuation has a regular trend, a second section 415b also relates to stone 12 and the attenuation has a higher peak at the stone 12 itself.

For the second section 415b, FIG. 5 shows in the same graph the detected trend (continuous line) and the reference trend (dashed line), whilst FIG. 6 shows the deviation between the detected trend and the reference trend.

The two points where the deviations is largest are respectively labelled $X_{1S}$ and $X_{2S}$ and correspond to the discontinuity caused by the stone: they correspond to projections of edges of the stone 12 in the corresponding slice of fruit 1. Therefore, the search for those points of largest deviation allows identification of the edges of the stone 12 in the respective section 415.

By repeating the processing for all sections 415, it is possible to determine the borders of the entire stone 12 within the flesh 11.

In a similar way, by analysing the trend of the deviation and its extent, it is possible to search for any zones of decay in the fruit 1 and/or any zones where the stone 12 and the flesh 11 of the fruit 1 are detached (in particular when the fruit 1 is an avocado) and/or any zones where the peel and the flesh of the fruit are detached (in particular when the fruit is a citrus fruit).

In fact, it should be noticed that zones of decay, hollow detachment zones and the peel have their own attenuation coefficients which are different from the attenuation coefficients of the flesh and the stone, therefore their effects on the attenuation may be identified in a similar way to what is described above for the stone.

A second mode of carrying out the method is described below.

Similarly to the first mode described above, for each section 415 two end points which correspond to the projection of the outer contour (that is to say, the outer surface of the peel) of the fruit 1 are determined and the radius of the corresponding slice of the fruit is determined, calculated as half-distance between the two end points of the section 415 assuming that the corresponding slice of the fruit has a circular shape with the radius calculated in this way.

For each point between the two end points of the section 415, a local coefficient of average attenuation is calculated by dividing the respective calculated value of X-ray signal attenuation (obtained by processing the X-ray image) by the length of the respective stretch of fruit passed through. The length of the respective stretch of fruit passed through is calculated as $L(x)=2 \cdot \sqrt{R^2-x^2}$, where R is the calculated radius, x is the distance of the point from the projection 410 of the axis of rotational symmetry 10, L(x) is the length for the point at distance x. See FIG. 7, which shows the lengths $L_1$ and $L_2$ for two respective points at distance $x_1$ and $x_2$.

In practice, that local coefficient of average attenuation is the average value of the attenuation coefficient relative to the specific stretch (with length L) of fruit passed through. For example, if the stretch comprises only flesh, the local coefficient of average attenuation corresponds to the attenuation coefficient for the flesh; if the stretch comprises both flesh and stone, the local coefficient of average attenuation corresponds to an intermediate value between the attenuation coefficient for the flesh and the attenuation coefficient for the stone.

Then a trend of the calculated local coefficient of average attenuation and its deviation relative to a trend with constant value is examined, in order to identify any anomalies, discontinuities or variations which are indicative of respective non-uniformities in the corresponding slice of fruit.

In fact, if the section 451 only comprises flesh, then the local coefficient of average attenuation remains substantially constant in the section; if there are zones of decay or stone present, these can be identified with criteria similar to those described above for the first mode of carrying out the method.

FIGS. 8 to 10 show images representing the local coefficient of average attenuation in three different avocado fruits. The regions 412 corresponding to the stones 12 (in which the local coefficient of average attenuation is higher than the region 411 of only flesh), as well as regions of decay 413 and detachment regions 414 (in which the local coefficient of average attenuation is lower than for the region 411 of only flesh), can be noticed. The method described above allows those regions to be identified.

An apparatus 9 configured for implementing the method for non-destructive inspection according to this disclosure is shown, in a schematic and simplified way, in FIG. 11.

The apparatus 9 comprises a movement device 91 (for example a conveyor belt) configured for moving the fruits 1 along a conveying path.

The apparatus 9 also comprises a positioning device 92 which is configured for positioning each fruit 1 in such a way that its axis of rotational symmetry 10 has an orientation that is substantially parallel to the predetermined plane 20. In particular, the predetermined plane 20 is a horizontal plane defined by the movement device 91. Moreover, in one specific embodiment, the positioning device 92 is configured for positioning each fruit 1 in such a way that its axis of rotational symmetry 10 is perpendicular to the movement direction along the conveying path that is defined by the movement device 91, as shown in FIG. 12. For example, the positioning device 92 may comprise biconical rollers independently controlled with feedback based on a video camera 94 which observes from above.

The apparatus 9 comprises an X-ray apparatus 93 for radiographing the fruit 1. The direction of emission of X-rays is substantially perpendicular to said predetermined plane 20 and the X-ray image obtained lies on said predetermined plane 20, being a projection on the latter.

The apparatus 9 comprises an electronic processing unit 95 which is configured for processing the X-ray image obtained and for carrying out the subsequent processing steps according to the method for non-destructive inspection of this disclosure.

As regards the positioning device 92, several variants are possible, referred to herein. In the case of fruit boxes with alveolar trays, it is possible to use a system with biconical rollers independently controlled with feedback based on a video camera which observes from above. In this case, the fruits are aligned, then gathered by suction cup systems from above and placed on the fruit box. After the fruits have been positioned oriented on the fruit box, it is possible to acquire an image during the passage of the whole fruit box. In the case of a grading machine, it is possible to use a system simply based on biconical rollers rotating during feeding. In this case, the chain which drives the rollers should not be below the rollers, but rather at the side of them, and the biconical rollers should be plastic and/or rubber. The rollers will be made to rotate during a feeding stretch in such a way as to align the fruit. Then the rotation is stopped during the X-ray scan.

Another possibility is putting the system under a roller table. A roller table is constituted of a series of rows of biconical rollers with a single axis. In this case, only the central axis of the rollers is metal, but it is far from the central part of the fruits.

The subject-matter described above may be modified and adapted in several ways without thereby departing from the scope of the appended claims.

All details may be substituted with other technically equivalent elements and the materials used, as well as the shapes and dimensions of the various components, may vary according to requirements.

The invention claimed is:

1. A method for non-destructive inspection of a fruit (1) having an axis of rotational symmetry (10), comprising the steps of:
    positioning the fruit (1) in such a way that its axis of rotational symmetry (10) has an orientation that is substantially parallel to a predetermined plane (20);
    radiographing the fruit (1), wherein X-rays are emitted with a direction of emission that is substantially perpendicular to said predetermined plane (20) and wherein an X-ray image obtained (41) lies on said predetermined plane (20), being a projection on said predetermined plane (20);
    processing the X-ray image obtained (41) to calculate, at corresponding points of the X-ray image (41), respective values of attenuation of X-ray signal through the fruit (1);
    dividing the X-ray image (41) into a plurality of sections (415) which are perpendicular to a projection (410) of the axis of rotational symmetry (10) on the predetermined plane (20), each section (415) being a projection of a corresponding slice of the fruit (1) that is substantially perpendicular to the axis of rotational symmetry (10);
and wherein, for each section (415), the method comprises the sub-steps of:
    determining two end points corresponding to a projection of an outer contour of the fruit (1), each end point being identifiable as a border between a region with null attenuation of the X-ray signal and a region with increasing or decreasing attenuation of the X-ray signal;

from the respective values calculated by processing the X-ray image obtained (41), obtaining a trend, between the two end points, of the attenuation of the X-ray signal;

calculating a reference trend, between the two end points, of the attenuation of the X-ray signal, adopting an attenuation coefficient having a value that is constant for the corresponding slice of the fruit (1);

between the two end points, calculating a deviation between the obtained trend of the attenuation of the X-ray signal and the reference trend;

examining a trend of the deviation, between the two end points, in order to identify any anomalies, discontinuities or variations which are indicative of respective non-uniformities in the corresponding slice of fruit (1).

2. The method for non-destructive inspection according to claim 1, wherein calculation of the reference trend between the two end points comprises the sub-steps of:

determining a radius (R) of the corresponding slice of the fruit (1), the radius (R) being calculated as half-distance between the two end points of the section (415);

for each point between the two end points of the section (415), calculating an attenuation reference value as $a_{ref}(x) = A \cdot (\sqrt{R^2 - x^2})/R$, where R is the calculated radius, x is distance of the point from the projection (410) of the axis of rotational symmetry (10), A is a constant, $a_{ref}(x)$ is the attenuation reference value at the point at distance x.

3. The method for non-destructive inspection according to claim 2, wherein the constant A has a value which is the largest attenuation value in the respective section (415), as obtained by processing the X-ray image (41).

4. The method for non-destructive inspection according to claim 1, wherein the attenuation of the X-ray signal is a quantity with a logarithmic dependence on the signal measured, in particular wherein the attenuation value a of the X-ray signal at a point x is calculated as $$a(x) = \log\left[\frac{I_e(x) - I_0(x)}{I(x) - I_0(x)}\right],$$

where I(x) is the signal measured at the point x in the presence of the fruit, $I_0(x)$ is the signal measured at the point x when X-ray emitter is switched off, $I_e(x)$ is the signal measured at the point x in the absence of the fruit.

5. The method for non-destructive inspection according to claim 1, wherein a position of the projection (410) of the axis of rotational symmetry (10) in the X-ray image (41) is calculated as axis of symmetry of the X-ray image (41) or as axis of symmetry of the projection of the outer contour of the fruit (1).

6. The method for non-destructive inspection according to claim 1, the fruit (1) having a stone (12), wherein in each section (415) two points where the deviation is largest are searched for, said two points corresponding to projections of edges of the stone (12) in the corresponding slice of the fruit (1).

7. The method for non-destructive inspection according to claim 6, wherein the non-destructive inspection is or comprises a search for size of the stone (12) in the fruit (1), in particular the fruit being an avocado.

8. The method for non-destructive inspection according to claim 1, wherein the non-destructive inspection is or comprises a search for any zones of decay in the fruit (1) and/or a search for any zones of detachment between a stone (12) and a flesh (11) of the fruit (1), in particular the fruit being an avocado, and/or a search for any zones of detachment between a peel and a flesh of the fruit, in particular the fruit being a citrus fruit.

9. A method for non-destructive inspection of a fruit (1) having an axis of rotational symmetry (10), comprising the steps of:

positioning the fruit (1) in such a way that its axis of rotational symmetry (10) has an orientation that is substantially parallel to a predetermined plane (20);

radiographing the fruit (1), wherein X-rays are emitted with a direction of emission that is substantially perpendicular to said predetermined plane (20) and wherein an X-ray image obtained (41) lies on said predetermined plane (20), being a projection on said predetermined plane (20);

processing the X-ray image obtained (41) to calculate, at corresponding points of the X-ray image (41), respective values of attenuation of X-ray signal through the fruit (1);

dividing the X-ray image (41) into a plurality of sections (415) which are perpendicular to a projection (410) of the axis of rotational symmetry (10) on the predetermined plane (20), each section (415) being a projection of a corresponding slice of the fruit (1) that is substantially perpendicular to the axis of rotational symmetry (10);

and wherein, for each section (415), the method comprises the sub-steps of:

determining two end points corresponding to a projection of an outer contour of the fruit (1), each end point being identifiable as a border between a region with null attenuation of the X-ray signal and a region with increasing or decreasing attenuation of the X-ray signal;

determining a radius (R) of the corresponding slice of the fruit (1), the radius (R) being calculated as half-distance between the two end points of the section (415);

for each point between the two end points of the section, calculating a local coefficient of average attenuation by dividing the respective calculated value of X-ray-signal attenuation by length (L) of the respective stretch of fruit passed through, the length (L) of the respective stretch of fruit passed through being calculated as $L(x) = 2 \cdot \sqrt{R^2 - x^2}$, where R is the calculated radius, x is distance of the point from the projection (410) of the axis of rotational symmetry (10), L(x) is the length for the point at distance x;

examining a trend of the calculated local coefficient of average attenuation and its deviation relative to a trend with constant value, in order to identify any anomalies, discontinuities or variations which are indicative of respective non-uniformities in the corresponding slice of fruit.

10. The method for non-destructive inspection according to claim 9, wherein the attenuation of the X-ray signal is a quantity with a logarithmic dependence on the signal measured, in particular wherein the attenuation value a of the X-ray signal at a point x is calculated as $$a(x) = \log\left[\frac{I_e(x) - I_0(x)}{I(x) - I_0(x)}\right],$$

where I(x) is the signal measured at the point x in the presence of the fruit, $I_0(x)$ is the signal measured at the point x when X-ray emitter is switched off, $I_e(x)$ is the signal measured at the point x in the absence of the fruit.

11. The method for non-destructive inspection according to claim 9, wherein a position of the projection (410) of the axis of rotational symmetry (10) in the X-ray image (41) is calculated as axis of symmetry of the X-ray image (41) or as axis of symmetry of the projection of the outer contour of the fruit (1).

12. The method for non-destructive inspection according to claim 9, the fruit (1) having a stone (12), wherein in each section (415) two points where the deviation is largest are searched for, said two points corresponding to projections of edges of the stone (12) in the corresponding slice of the fruit (1).

13. The method for non-destructive inspection according to claim 12, wherein the non-destructive inspection is or comprises a search for size of the stone (12) in the fruit (1), in particular the fruit being an avocado.

14. The method for non-destructive inspection according to claim 9, wherein the non-destructive inspection is or comprises a search for any zones of decay in the fruit (1) and/or a search for any zones of detachment between a stone (12) and a flesh (11) of the fruit (1), in particular the fruit being an avocado, and/or a search for any zones of detachment between a peel and a flesh of the fruit, in particular the fruit being a citrus fruit.

15. An apparatus (9) for carrying out a non-destructive inspection of a fruit (1) having an axis of rotational symmetry (10),
the apparatus (9) being configured for implementing a method for non-destructive inspection of the fruit (1), the apparatus comprising:
a movement device (91) configured for moving the fruit (1) along a conveying path;
a positioning device (92) configured for positioning the fruit (1) in such a way that the axis of rotational symmetry (10) of the fruit (1) has an orientation that is substantially parallel to a predetermined plane (20);
an X-ray apparatus (93) for radiographing the fruit (1), wherein a direction of emission of X-rays is substantially perpendicular to said predetermined plane (20) and wherein an X-ray image obtained (41) lies on said predetermined plane (20), being a projection on said predetermined plane (20);
an electronic processing unit (95) configured for processing the X-ray image obtained (41),
wherein the electronic processing unit (95) is configured for carrying out the following processing steps:
calculating, at corresponding points of the X-ray image (41), respective values of attenuation of X-ray signal through the fruit (1);
dividing the X-ray image (41) into a plurality of sections (415) which are perpendicular to a projection (410) of the axis of rotational symmetry (10) on the predetermined plane (20), each section (415) being a projection of a corresponding slice of the fruit (1) that is substantially perpendicular to the axis of rotational symmetry (10);
wherein the electronic processing unit (95) is configured for carrying out the following processing sub-steps for each section (415):

determining two end points corresponding to a projection of an outer contour of the fruit (1), each end point being identifiable as a border between a region with null attenuation of the X-ray signal and a region with increasing or decreasing attenuation of the X-ray signal;
from the respective values calculated by processing the X-ray image obtained (41), obtaining a trend, between the two end points, of the attenuation of the X-ray signal;
calculating a reference trend, between the two end points, of the attenuation of the X-ray signal, adopting an attenuation coefficient having a value that is constant for the corresponding slice of the fruit (1);
between the two end points, calculating a deviation between the obtained trend of the attenuation of the X-ray signal and the reference trend;
examining a trend of the deviation, between the two end points, in order to identify any anomalies, discontinuities or variations which are indicative of respective non-uniformities in the corresponding slice of fruit (1);
and/or
wherein the electronic processing unit (95) is configured for carrying out the following processing sub-steps for each section (415):
determining two end points corresponding to a projection of an outer contour of the fruit (1), each end point being identifiable as a border between a region with null attenuation of the X-ray signal and a region with increasing or decreasing attenuation of the X-ray signal;
determining a radius (R) of the corresponding slice of the fruit (1), the radius (R) being calculated as half-distance between the two end points of the section (415);
for each point between the two end points of the section, calculating a local coefficient of average attenuation by dividing the respective calculated value of X-ray-signal attenuation by length (L) of the respective stretch of fruit passed through, the length (L) of the respective stretch of fruit passed through being calculated as $L(x)=2\cdot\sqrt{R^2-x^2}$, where R is the calculated radius, x is distance of the point from the projection (410) of the axis of rotational symmetry (10), L(x) is the length for the point at distance x;
examining a trend of the calculated local coefficient of average attenuation and its deviation relative to a trend with constant value, in order to identify any anomalies, discontinuities or variations which are indicative of respective non-uniformities in the corresponding slice of fruit.

16. The apparatus (9) according to claim 15, wherein the positioning device (92) is configured for positioning each fruit (1) in such a way that the axis of rotational symmetry (10) of the fruit (1) is substantially parallel to the predetermined plane (20) and perpendicular to a movement direction along the conveying path that is defined by the movement device (91).

* * * * *